United States Patent
Koo et al.

(10) Patent No.: US 12,064,536 B2
(45) Date of Patent: Aug. 20, 2024

(54) PHOTOCATALYST FOR AIR PURIFICATION, AND CERAMIC CATALYST FILTER AND AIR PURIFICATION DEVICE INCLUDING THE SAME

(71) Applicant: Samsung Electronics Co., Ltd., Suwon-si (KR)

(72) Inventors: Minseok Koo, Suwon-si (KR); Hyukjae Kwon, Suwon-si (KR); Hyun Chul Lee, Hwaseong-si (KR); Sukeun Kuk, Suwon-si (KR); Dongsik Yang, Seoul (KR); Sehyeong Oh, Seoul (KR); Sangmin Ji, Yongin-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 616 days.

(21) Appl. No.: 17/379,871

(22) Filed: Jul. 19, 2021

(65) Prior Publication Data
US 2022/0280677 A1    Sep. 8, 2022

(30) Foreign Application Priority Data

Mar. 8, 2021 (KR) .................. 10-2021-0030420

(51) Int. Cl.
*A61L 9/20* (2006.01)
*B01D 39/20* (2006.01)
(Continued)

(52) U.S. Cl.
CPC .......... *A61L 9/205* (2013.01); *B01D 39/2068* (2013.01); *B01D 53/86* (2013.01);
(Continued)

(58) Field of Classification Search
CPC ...... A61L 9/205; A61L 2209/14; B01J 35/39; B01J 21/06; B01J 23/72; B01J 27/12;
(Continued)

(56) References Cited

U.S. PATENT DOCUMENTS 8,518,848 B2   8/2013  Taniguchi et al.
8,551,906 B2   10/2013  Lu et al.
(Continued)

FOREIGN PATENT DOCUMENTS

CN  101524642 A   9/2009
EP  3670580 A1   6/2020
(Continued)

OTHER PUBLICATIONS

English Abstract of CN 101524642.
English Abstract of KR 10-2016-0001608 (also published as KR 101731392 B1).

*Primary Examiner* — Lessanework Seifu
(74) *Attorney, Agent, or Firm* — CANTOR COLBURN LLP

(57) ABSTRACT

A photocatalyst for air purification, a photocatalyst film including the photocatalyst, and an air purification device including the photocatalyst. The photocatalyst for air purification includes: a first metal oxide particle having ultraviolet absorptivity, and fluorine bound to a surface of the first metal oxide particle; second metal oxide particles present on the surface of the first metal oxide particle. The use of the photocatalyst for air purification to remove or degrade volatile organic compounds (VOCs) and viruses.

20 Claims, 17 Drawing Sheets

(51) Int. Cl.
  *B01D 53/86* (2006.01)
  *B01J 35/39* (2024.01)
  *C01G 23/053* (2006.01)

(52) U.S. Cl.
  CPC ............ *B01J 35/39* (2024.01); *C01G 23/053* (2013.01); *A61L 2209/14* (2013.01); *B01D 2201/18* (2013.01); *B01D 2255/802* (2013.01); *B01D 2258/06* (2013.01); *C01P 2004/64* (2013.01)

(58) Field of Classification Search
  CPC ....... B01J 37/02; B01J 37/08; B01D 39/2068; B01D 53/86; B01D 2201/18; B01D 2255/20707; B01D 2255/20761; B01D 2255/707; B01D 53/8668; B01D 2239/0464; B01D 2239/0478; B01D 2255/802; B01D 2257/708; B01D 2257/91; B01D 2259/804; B01D 2239/10; C01G 23/053; C01G 3/02; C01P 2004/64; C01P 2002/54; C01P 2002/82; C01P 2004/82; C01P 2006/12

See application file for complete search history.

(56) References Cited

U.S. PATENT DOCUMENTS

| | | | |
|---|---|---|---|
| 2010/0135864 A1* | 6/2010 | Taniguchi | B01J 27/135 |
| | | | 502/77 |
| 2017/0274364 A1 | 9/2017 | Idriss et al. | |
| 2021/0094026 A1* | 4/2021 | Kwon | A61L 9/205 |

FOREIGN PATENT DOCUMENTS

| | | |
|---|---|---|
| KR | 1017031392 B1 | 4/2017 |
| KR | 10-2021-0039201 A | 4/2021 |
| WO | 2016030753 A1 | 3/2016 |

* cited by examiner

1

PHOTOCATALYST FOR AIR PURIFICATION, AND CERAMIC CATALYST FILTER AND AIR PURIFICATION DEVICE INCLUDING THE SAME

CROSS-REFERENCE TO RELATED APPLICATION

This application claims priority under 35 U.S.C. § 119 to Korean Patent Application No. 10-2021-0030420, filed on Mar. 8, 2021, in the Korean Intellectual Property Office, the content of which is herein incorporated by reference in its entirety.

BACKGROUND

1. Field

The present disclosure relates to photocatalysts for air purification, and photocatalyst films and air purification devices including the photocatalysts.

2. Description of the Related Art

To remove pollutants from the air, methods of absorbing/removing gaseous pollutants with an adsorbent (for example, active carbon) having a large specific surface area in conjunction with an air cleaning filter are known. A method of decomposing gaseous pollutants into carbon dioxide by using a photocatalyst has also been described. When a photocatalyst is exposed to light of sufficient energy electrons and holes form in the photocatalyst. The electrons and holes induce oxidation/reduction reactions with the gaseous pollutants resulting in the decomposition or degradation (or removal from air) of the gaseous pollutants. In the case of a virus, when a virus comes in contact with a metal material such as copper, the virus may be killed by an oligodynamic effect, that is, a phenomenon in which small amounts of a heavy metal material may inhibit the growth of the virus or may kill the virus.

However, known adsorption/removal techniques have technical disadvantages including adsorbed gaseous pollutants once desorbed from the adsorbent may lead to secondary pollution, or a separate regeneration step such as heating to a high temperature is often necessary to replenish (or reactivate) the adsorbent, or the replenished adsorbent may have a relatively short lifetime, and thus, requires frequent replacement.

In the related art, gaseous pollutant removal techniques using photocatalysts are disadvantageous in that the generated electrons and holes may rapidly combine prior to coming in contact with a gaseous pollutant, and thus the efficiency of the photocatalyst is reduced. In addition, intermediate materials generated by the decomposition of gaseous pollutants may be adsorbed on the surface of a catalyst, thereby reducing the efficiency of the catalyst.

Accordingly, there is a need for a continuous air purification technology that does not cause secondary pollution due to desorption of pollutants, does not require a separate regeneration step such as high-temperature heating, or can increase the efficiency of the oxidation/reduction reaction with the pollutant.

SUMMARY

Provided are photocatalysts for air purification having excellent decomposition efficiency of gaseous pollutants.

Provided are ceramic catalyst filters including the photocatalysts.

Provided are air purification devices including the photocatalysts.

Additional aspects will be set forth in part in the description which follows and, in part, will be apparent from the description, or may be learned by practice of the presented embodiments of the disclosure.

According to an aspect of an embodiment, a photocatalyst for air purification includes a first metal oxide particle having ultraviolet absorptivity, and fluorine bound to the surface of the first metal oxide particle; and second metal oxide particles present on the surface of the first metal oxide particle.

According to an aspect of an embodiment, a ceramic catalyst filter including: a monolithic structure having a first surface that blocks a first material though provides transmission of a second material, and a second surface from which the second material is removed or degraded. The second surface of the monolithic structure includes a catalyst layer including a photocatalyst for removing the second material upon exposure to ultraviolet light. The photocatalyst includes a first metal oxide particle having ultraviolet absorptivity, and fluorine bound to a surface of the first metal oxide particle, and second metal oxide particles present on the surface of the first metal oxide particle.

According to an aspect of an embodiment, a method of preparing the photocatalyst, the method including: conducting a first heat treatment of a mixture including a precursor of a first metal oxide particle having ultraviolet absorptivity, and a precursor of a second metal oxide particles, to obtain a first product; adding glucose and sodium hydroxide to the first product and conducting a second heat treatment to obtain a second product; and fluorinating a surface of the second product.

According to an aspect of another embodiment, a ceramic catalyst filter includes the photocatalyst for air purification.

According to an aspect of another embodiment, an air purification device includes the photocatalyst for air purification.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
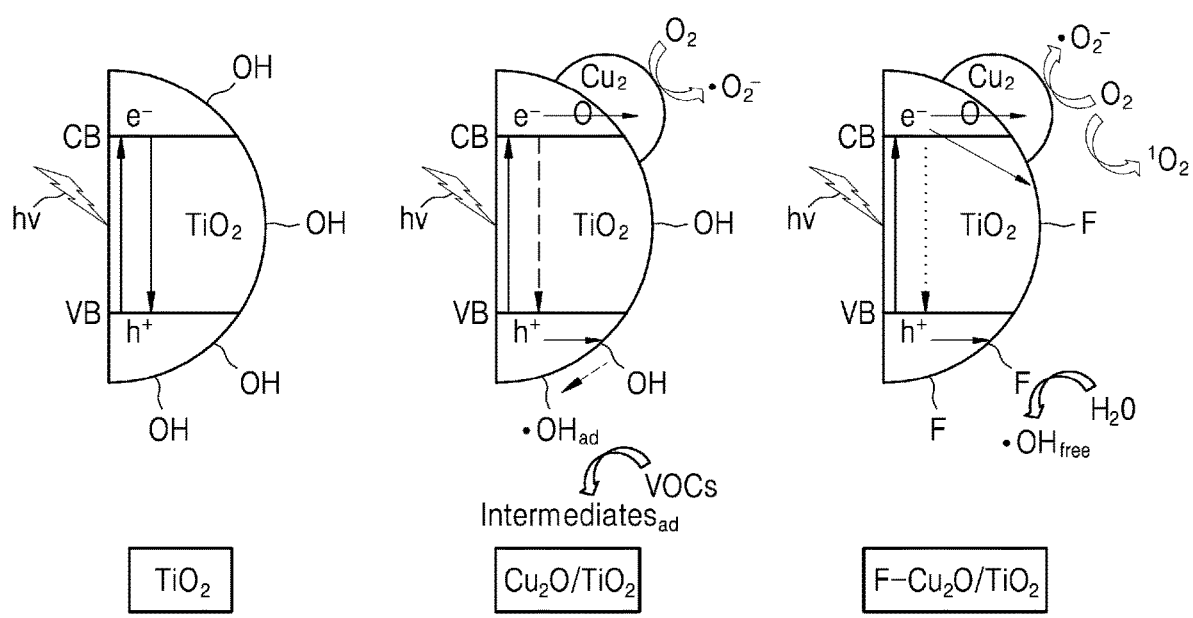
FIG. 1 is a proposed schematic model of the surface photochemistry of a photocatalyst for air purification according to an embodiment.

The present inventive concept will now be described more fully with reference to the accompanying drawings, in which example embodiments are illustrated, and wherein like reference numerals refer to like elements throughout. However, the present inventive concept may be embodied in many different forms, should not be construed as being limited to the embodiments set forth herein, and should be construed as including all modifications, equivalents, and alternatives within the scope of the present inventive concept.

The terms used herein is for the purpose of describing particular embodiments only and is not intended to be limiting of the inventive concept. Singular expressions include plural expressions including "at least one," unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the slash "/" or the term "and/or" includes any and all combinations of one or more of the associated listed items.

In the drawings, the thickness is enlarged or reduced in order to clearly express various layers and regions. Throughout the specification, the same reference numerals are attached to similar parts Throughout the specification, when an element such as a layer, a film, a region or a component is referred to as being "on" another layer or element, it can be "directly on" the other layer or element, or intervening layers, regions, or components may also be present. In contrast, when an element is referred to as being "directly on" another element, there are no intervening elements present.

Terms "first", "second", "third", etc., may be used herein to describe various elements, components, regions, and/or layers, these elements, components, regions, and/or layers should not be limited by these terms. These terms are used only to distinguish one component from another, not for purposes of limitation. Thus, "a first element," "component," "region," "layer," or "section" discussed below could be termed a second element, component, region, layer, or section without departing from the teachings herein.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. Further, it will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. Alternatively, it will be further understood that the terms will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% of the stated value.

Exemplary embodiments are described herein with reference to cross-sectional views that are schematic illustrations of ideal embodiments. As such, variations from the shape of the illustration as a result of, for example, manufacturing techniques and/or tolerances should be expected. Accordingly, the embodiments described herein should not be construed as limited to specific shapes of regions as illustrated herein, but should include variations in shapes resulting from, for example, manufacturing. For example, regions depicted as flat may typically have rough and/or non-linear features. Moreover, the sharp angles illustrated may be rounded. Accordingly, the regions shown in the figures are schematic in nature, and their shapes are not intended to illustrate the precise shapes of the regions, and are not intended to limit the scope of the claims.

Hereinafter, a photocatalyst for air purification according to an embodiment, a photocatalyst filter including the photocatalyst, and an air purification device including the photocatalyst will be described in detail.

A photocatalyst for air purification according to an embodiment includes a first metal oxide particle having ultraviolet absorptivity, and fluorine bound to a surface of the first metal oxide particle; and second metal oxide particles present on a surface of the first metal oxide particle.

FIG. 1 is a proposed schematic model of the surface photochemistry of a photocatalyst for air purification according to an embodiment. Referring to FIG. 1, the first metal oxide particle is a carrier upon which second metal oxide particles are present, e.g., the second metal oxide particles may be supported by the first metal oxide particle, and includes, for example, a metal oxide such as $TiO_2$ capable of absorbing ultraviolet light. When the first metal oxide particle is exposed to ultraviolet light, electrons and holes are generated, which can then be used to decompose/degrade gaseous pollutants by inducing oxidation/reduction reactions at or near the surface of the photocatalyst. In the first metal oxide surface upon which the second metal oxide particles and fluorine are present, electrons excited by ultraviolet light are recombined with a valence band.

In the photocatalyst for air purification, the second metal oxide particles are present or supported on a surface of the first metal oxide, and fluorine is bound to the surface of the first metal oxide particle. For example, the fluorine may be bonded to a surface of the first metal oxide particle. In the photocatalyst, the electrons generated by ultraviolet light may be stored or stabilized by the second metal oxide particles and/or fluorine without being recombined with a valence band. The result of which is an increase in the production efficiency of forming reactive oxygen species (ROS) through the reduction of oxygen, and thereby, effectively cause the removal or degradation of VOCs or viruses. The fluorine bound to the surface of the first metal oxide particle may increase the generation of ROS to increase the decomposition (or degradation) efficiency of VOCs, and may inhibit the adsorption of intermediates produced by removing VOCs on the surface of the photocatalyst to continuously remove, decompose, or degrade the VOCs.

In the photocatalyst for air purification according to an embodiment, the fluorine bound to the surface of the first metal oxide particle is present in a region other than a region in which the second metal oxide particles are present, and the fluorine is also not present at an interface between the first metal oxide particle and the second metal oxide particles.

In the photocatalyst for air purification, the first metal oxide particle is first mixed with the second metal oxide particles, and then, the mixture is surface-fluorinated. As a result, fluorine is not present at an interface between the first metal oxide particle and the second metal oxide particles. In contrast, if the first metal oxide particle is surface-fluorinated, and then mixed with the second metal oxide particles, it is difficult for the second metal oxide particle to become bound to the surface of the first metal oxide particle.

As described above, the first metal oxide particle may be considered as a support or carrier for the second metal oxide particles. The first metal oxide particle may include a metal oxide capable of absorbing ultraviolet light. According to an embodiment, the first metal oxide particle may include metal oxides of titanium (Ti), zinc (Zn), zirconium (Zr), tantalum (Ta), niobium (Nb), tungsten (W), or an alloy of metal oxides thereof. For example, the first metal oxide particle may include titanium oxide such as $TiO_2$.

The first metal oxide particle may have a specific surface area of about 20 square meters per gram ($m^2/g$) to about 300 $m^2/g$. For example, the first metal oxide particle may have a specific surface area of about 30 $m^2/g$ to about 250 $m^2/g$. For example, the first metal oxide particle may have a specific surface area of about 50 $m^2/g$ to about 230 $m^2/g$. Without being limited in theory, the large surface area within the above range can provide a sufficient level of adsorption efficiency for the VOCs, which may then lead to an increase in decomposition efficiency of the VOCs. As the specific surface area of the first metal oxide particle increases, the adsorption efficiency of VOC may increase, and the decomposition efficiency of the VOCs may also increase.

The first metal oxide particle may be a primary particle, or may be a secondary particle in which primary particles are aggregated or bonded to each other. The average particle diameter of primary particles may be about 0.1 nanometers (nm) to about 20 nm, for example, about 1 nm to about 10 nm, for example, about 3 nm to about 7 nm. The average particle diameter of secondary particles in which primary particles are aggregated may be about 10 nm to about 200 nm, for example, about 30 nm to about 150 nm, for example, about 50 nm to about 100 nm. Within the above range, the first metal oxide particle may obtain a desired level of specific surface area.

The second metal oxide particles are present on or supported on a surface of the first metal oxide particle.

The second metal oxide particle may improve light absorption, absorb electrons generated by light (e.g., ultraviolet light) to minimize or prevent recombination of electron-hole charge pairs, and reduce the resistance of the catalyst to facilitate charge transfer.

Further, the second metal oxide particles may exhibit a virus removal effect by an oligodynamic effect (that is, a phenomenon in which the ionic action of relatively small amounts of a heavy metal material may inhibit the growth of the virus, or under select conditions, kill the virus.

According to an embodiment, the second metal oxide particles may include at least one second metal oxide copper (Cu), platinum (Pt), gold (Au), silver (Ag), zinc (Zn), palladium (Pd), or an alloy of metal oxides thereof. Moreover, at least one second metal oxide particle of the second metal oxide particles is different from the first metal oxide particle. For example, the second metal oxide particle may include $Cu_2O$. Because copper (I) oxide ($Cu_2O$) is more active than copper (II) oxide (CuO), the former can induce a highly efficient reduction reaction as a p-type semiconductor photocatalyst.

According to an embodiment, the content of the second metal oxide particles may be about 0.1 parts by weight to about 5 parts by weight based on 100 parts by weight of the first metal oxide particle. Within the above range, the absorption rate of light of the photocatalyst may be improved, and the resistance of the photocatalyst may be lowered to facilitate the transfer of charges, and thereby, improving the decomposition efficiency of VOCs.

The average particle diameter of the second metal oxide particles may be about 5 nm to about 10 nm. Within the above range, it is possible to obtain a photocatalyst for air purification with improved photocatalytic reactivity, and to provide for the second metal oxide particles to be supported by the first metal oxide particle.

According to an embodiment, the first metal oxide particle may be a microscale primary particle or microscale secondary particle (i.e., an aggregation, agglomeration or bound grouping of two or more primary particles), the second metal oxide particle may be a nanometer-scale primary particle, and the surface of the first metal oxide particle may be surrounded by the second metal oxide particles.

Regarding the particle shape, at least the majority (or all) of the first metal oxide particles and at least the majority (or all) of the second metal oxide particles may independently have a spherical shape, a tubular shape, a rod shape, a fiber shape, a sheet shape, a conical shape, a pyramidal shape, a toroidal shape, or any combined shape thereof. An example of a combined shape is a hemisphere combined with a cube. The at least a majority of the first metal oxide particles and the second metal oxide particles may have the same shape or a different shape in order to control the absorption efficiency of the photocatalyst for air purification.

In the photocatalyst for air purification, fluorine is bound to, e.g., bonded to, a surface of the first metal oxide particle.

In the case of a photocatalyst that is not surface-fluorinated, a functional group such as a hydroxy (—OH) group is bound to, e.g., bonded to, a surface of the first metal oxide particle. In this case, when the particle is excited by ultraviolet light, electrons are recombined in the valence band, the hydroxy (—OH) group itself may become $\cdot OH_{ad}$, and thus, reduce the efficiency of generating active oxygen species (ROS).

In contrast, in the photocatalyst for air purification, because a functional group on the surface of the first metal oxide particle includes fluorine, which is obtained by surface fluorination, the efficiency of generating active oxygen species (ROS) may be increased, and thus, the decomposition efficiency of VOCs may be increased, and the adsorption of intermediates generated by removing VOCs on the surface of the catalyst may be inhibited, and the photocatalyst may continuously remove/decompose VOC.

As described above, in the photocatalyst for air purification according to an embodiment, secondary pollution due to desorption is essentially non-existent, a separate regeneration process such as high-temperature heating may not be necessary, and the production efficiency of reactive oxygen species (ROS) may be increased through the reduction of oxygen to effectively remove/decompose/degrade VOCs or viruses.

The photocatalyst for air purification may be mounted in various indoor and outdoor air purification devices (for example, air purifiers, air purification facilities, and air conditioning facilities) in the form of a filter and applied as a VOC gas removal module. photocatalyst for air purification may also be applied to indoor and outdoor air cleaning systems for removing fine dust.

Furthermore, the photocatalyst for air purification may be used as a material for removing various gaseous pollutants, and may thus be applied to air purification devices and systems for not only removing air pollutants such as nitrogen oxides ($NO_x$), sulfur oxides ($SO_x$), ammonia ($NH_3$), odorous substances, bacteria, viruses, or other pathogens, but also for removing VOCs.

According to an embodiment, a ceramic catalyst filter capable of simultaneously removing particles and gases by coating a ceramic filter with the photocatalyst may be provided.

A ceramic catalytic filter according to an embodiment and a filtering system including the ceramic catalytic filter will be described in detail with reference to the accompanying drawings.

A ceramic catalytic filter according to an embodiment includes a monolithic structure having a first surface that blocks a first material though provides transmission of a second material, and a second surface from which the second material is removed or degraded, wherein the second surface of the monolithic structure comprises a catalyst layer including a photocatalyst for removing, degrading, or decomposing the second material upon exposure of the photocatalyst to ultraviolet light. The photocatalyst includes a first metal oxide particle having ultraviolet absorptivity, and fluorine bound to a surface of the first metal oxide particle, and second metal oxide particles present on, or supported by, the surface of the first metal oxide particle.

The monolithic structure may be porous. The entire monolithic structure may be a single ceramic material. Alternatively, the monolithic structure may be a catalyst material, and in this case, the second surface may be a photocatalytic material that is activated upon exposure to light energy, e.g., ultraviolet light.

The first and second surfaces may include surfaces that are parallel to each other, e.g., in a vertical, or horizontal direction.

The first material may include fine dust, and the second material may include a volatile organic compound (VOC).

Figure 13:
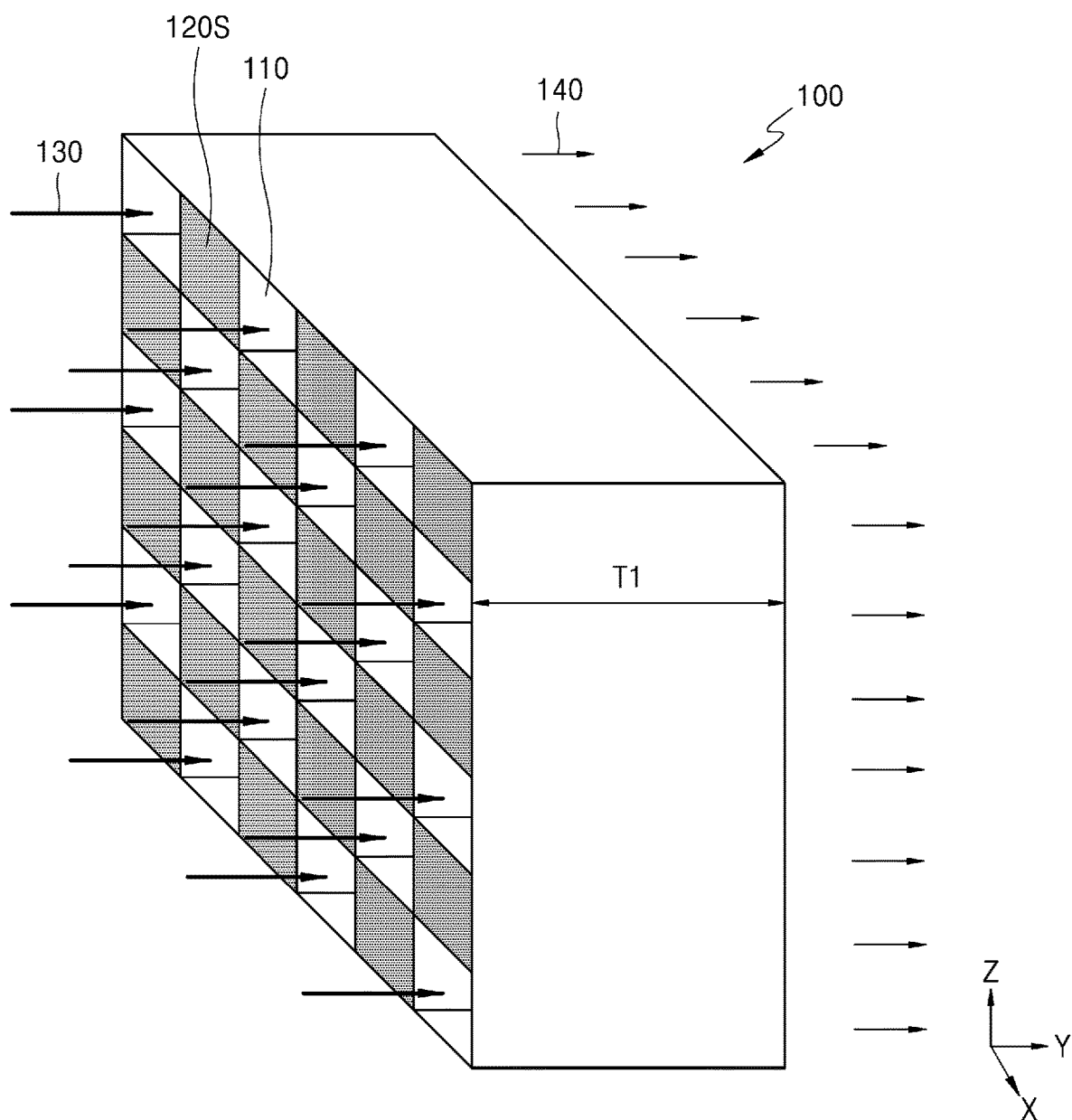
FIG. 13 is a perspective view of a ceramic catalyst filter according to an embodiment.

FIG. 13 illustrates a ceramic catalyst filter according to an embodiment. Referring to FIG. 13, a ceramic catalytic filter 100 includes an inlet surface through which a material 130 is introduced and an outlet surface through which a gas 140 is discharged. The material 130, e.g., indoor or outdoor air that may require purification, may include at least two kinds of materials including a first material and a second material that should be filtered, degraded, or removed. For example, the material 130 may include a particulate first material and a gaseous second material. The ceramic catalytic filter 100 has a thickness T1 given in a direction (Y-axis direction) in which the gas 140, e.g., purified air, exists from the filter 100 as a result of in-part the catalytic reaction of the ceramic catalytic filter. The ceramic catalyst filter 100 includes a plurality of first grooves or channels 110 each having an inlet in a direction in which the material 130 is introduced and an outlet in a direction (Y-axis direction) opposite the inlet. The material 130 is introduced into the ceramic catalyst filter 100 through the plurality of first grooves or channels 110. The plurality of first grooves or channels 110 are regularly arranged. The plurality of first grooves or channels 110 may be arranged in parallel to each other. The ceramic catalytic filter 100 includes a plurality of first surfaces 120S in a direction in which the material 130 is enters the filter and a gas 140 exits the filter. The plurality of first surfaces 120S are regularly arranged. The plurality of first surfaces 120S are disposed between the plurality of first grooves or channels 110. That is, one first surface 120S is located between the plurality of first grooves or channels 110 in the horizontal and vertical directions. In other words, one first groove or channel 110 exists between the plurality of first surfaces 120S in the horizontal and vertical directions. One first groove or channel 110 is surrounded by four first surfaces 120S, and one first surface 120S is surrounded by four first grooves or channels 110.

Figure 14:
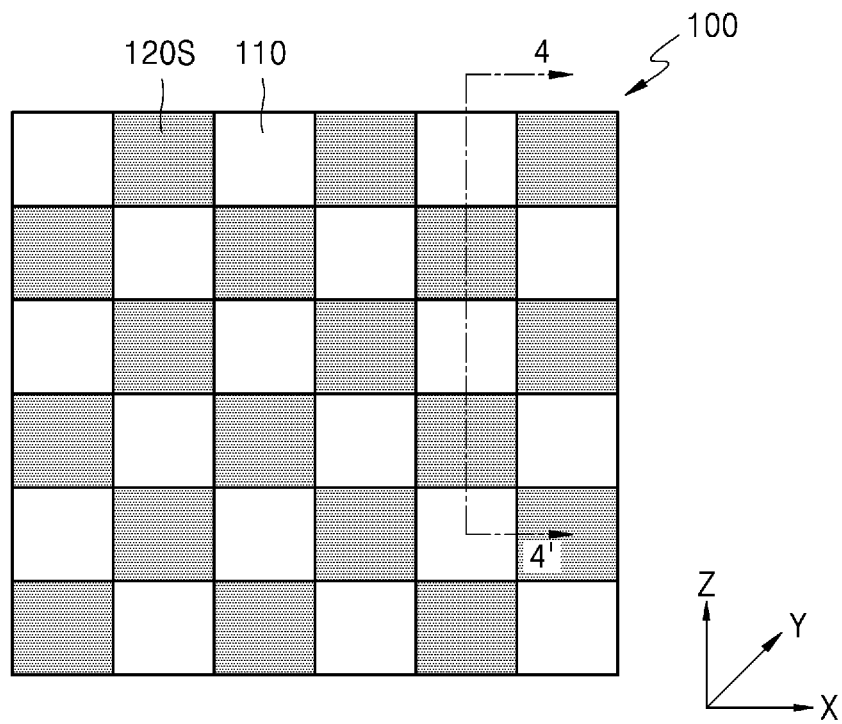
FIG. 14 is a view of an air inlet surface of the ceramic catalytic filter of FIG. 13.

FIG. 14 is a front view of an air inlet surface of the ceramic catalytic filter of FIG. 13.

Figure 15:
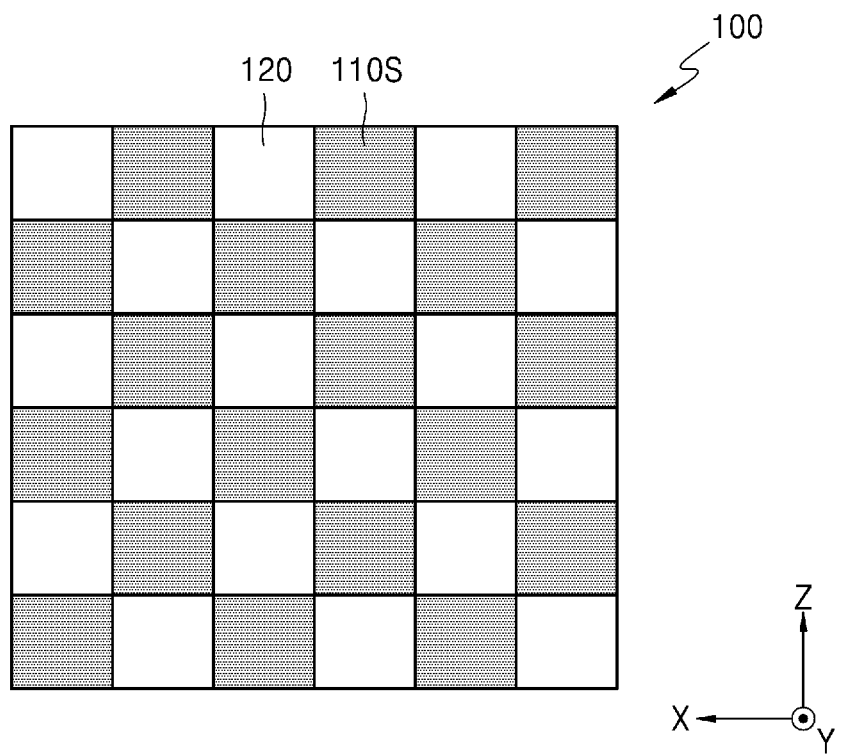
FIG. 15 is a view of an air outlet surface of the ceramic catalytic filter of FIG. 13.

FIG. 15 illustrates a rear surface of the ceramic catalytic filter 100, that is, a gas outlet surface. Referring to FIG. 15, the ceramic catalyst filter 100 includes a plurality of second grooves or channels 120 and a plurality of second surfaces 110S on the side from which gas is discharged. The plurality of second grooves or channels 120 serve as outlets through which gas 140 is discharged. The gas discharged through the second groove or channel 120 may be relatively clean or harmless gas in which harmful materials or impurities including the first or second materials have been filtered out of the material 130 such as a gas or air in need of purification. The plurality of second grooves or channels 120 are regularly arranged. The plurality of second surfaces 110S are also regularly arranged. The arrangement relationship between the plurality of second grooves or channels 120 and the plurality of second surfaces 110S may follow the arrangement relationship between the plurality of first grooves or channels 110 and the plurality of first surfaces 120S. The plurality of second surfaces 110S correspond to the plurality of first grooves or channels 110, and the plurality of second grooves or channels 120 correspond to the plurality of first surfaces 120S.

Referring to FIGS. 13 and 15 together, the second surface 110S serves as a back surface of the first groove or channel 110 and the first surface 120S serves as a front surface of the second groove or channel 120.

Figure 16:
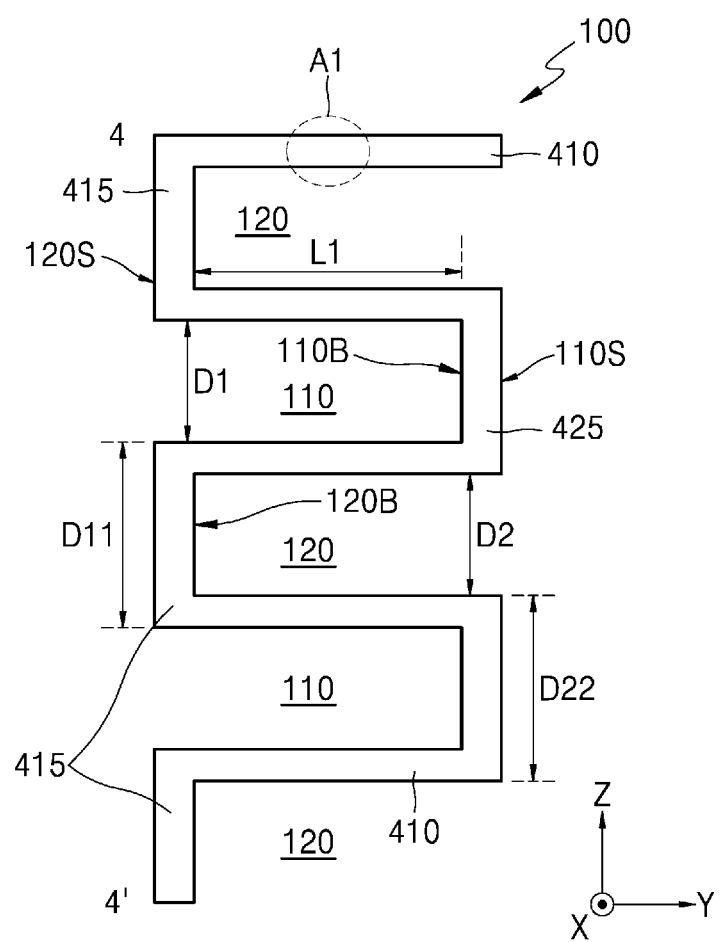
FIG. 16 is a cross-sectional view taken along the line 4-4' of FIG. 14.

FIG. 16 illustrates a cross-sectional view taken along the line 4-4' of FIG. 14. The ceramic catalyst filter 100 may be a monolithic structure or a monolithic frame. The ceramic catalyst filter 100 may have a frame formed entirely of a single material (for example, ceramic material, catalyst material, or the like). The ceramic catalyst filter 100 may be a single body connected as one, but for convenience of explanation, it will be divided into a horizontal portion and a vertical portion.

Referring to FIG. 16, the ceramic catalyst filter 100 may be a structure having a frame in which a plurality of first and second grooves or channels 110 and 120 are sequentially stacked in the Z-axis direction. As depicted in FIG. 16, the ceramic catalyst filter 100 includes a plurality of horizontal portions 410 and a plurality of vertical portions 415 and 425. Spatially, the plurality of horizontal portions 410 that are spaced apart in the Z-axis direction. Here, for convenience, the Z-axis direction is referred to as a vertical direction. The plurality of horizontal portions 410 are parallel to each other in the Y-axis direction. The plurality of horizontal portions 410 may have sections that are the same or different length. The Y-axis direction may be a direction in which the gas 140 generated as a result of the catalytic reaction is discharged from the filter 100. The Y axis is perpendicular to the Z axis. Here, for convenience, the Y-axis direction is regarded as the horizontal direction.

The plurality of vertical portions 415 and 425 are parallel to each other, and are spatially spaced apart from each other. The plurality of vertical portions 415 and 425 are disposed between the plurality of horizontal portions 410. The plurality of horizontal portions 410 are also disposed between the plurality of vertical portions 415 and 425. The plurality of horizontal portions 410 are connected to each other through the plurality of vertical portions 415 and 425. The plurality of vertical portions 415 and 425 are parallel to each other and are spatially spaced apart from each other. The plurality of vertical portions 415 and 425 are connected to each other through the plurality of horizontal portions 410. The plurality of vertical portions 415 and 425 include a plurality of first vertical portions 415 and a plurality of second vertical portions 425. The plurality of first vertical portions 415 and the plurality of second vertical portions 425 are spaced apart from each other in the Y-axis direction. The plurality of first vertical portions 415 are spaced apart from each other in the Z-axis direction, and are aligned in parallel in the Z-axis direction. The plurality of second vertical portions 425 are also spaced apart from each other in the Z-axis direction and are aligned in parallel in the Z-axis direction. The plurality of first vertical portions 415 are disposed at a side where the material 130 is introduced. The plurality of second vertical portions 425 are disposed at a side from which the gas 140 generated by a catalytic reaction is discharged.

The plurality of horizontal portions 410 may be a wall of the first or second grooves or channels 110 and 120. That is, the plurality of horizontal portions 410 is located between the first groove or channel 110 and the second groove or channel 120 to serve as a boundary disposed between the grooves or channels 110 and 120. The wall refers to a sidewall between the first and second grooves or channels 110 and 120. The thicknesses of the plurality of horizontal portions 410 may the same as each other, but may be different from each other. The thicknesses of the plurality of horizontal portions 410 may be the same or different as the thicknesses of the plurality of vertical portions 415 and 425. The horizontal portion 410, as the wall of the first groove or channel 110, is spaced apart by a first distance D1 in the Z-axis direction. The horizontal portion 410, as the wall of the second groove 120, is spaced apart by a first distance D2 in the Z-axis direction. In an embodiment, the first and second distances D1 and D2 may be the same or different than another. That is, the diameters of inlets and outlets of the first and second grooves or channels 110 and 120 may be the same or different. The lengths L1 of the plurality of horizontal portions 410 in the Y-axis direction may be the same or different than another. The depth of the first and second grooves or channels 110 and 120 may be determined by a length L1 of the horizontal portion 410 in the Y-axis direction. Accordingly, the depths of the first and second grooves or channels 110 and 120 may be the same or different than another. For example, in another embodiment, the depth of the first groove 110 may be different from the depth of the second groove or channel 120. The plurality of first vertical portions 415 may be a bottom of the second groove 120. The plurality of second vertical portions 425 may be a bottom of the first groove 110. The air permeability of the bottom of the first groove 110 may be different from the air permeability of the bottom of the second groove 120. The bottom of the second groove 120 may be configured to block a gaseous material. The diameter D11 of the first vertical portion 415 may be the same as the diameter D22 of the second vertical portion 425. The thicknesses of the first and second vertical portions 415 and 425 in the Y-axis direction may be the same.

The plurality of horizontal portions 410 and the plurality of vertical portions 415 and 425 are connected as a single body, and may be a ceramic material layer formed of a single ceramic material or catalytic material.

When a single body of ceramic material is used, the catalytic material may vary depending on the energy used to activate the ceramic catalyst filter 100.

As a first example, when the ceramic catalyst filter 100 is exposed to light energy, the catalytic material may be a metal compound capable of causing a photocatalytic reaction, for example, $TiO_2$ or $WO_3$. The light energy may include ultraviolet light energy or visible light energy.

As a second example, when electrical is applied to the ceramic catalyst filter 100, e.g., direct current (DC) or alternating current (AC), the catalytic material may be an electroconductive metal compound capable of an oxygen reduction reaction (ORR), which would take place in the plurality of horizontal portions 410 and/or the plurality of vertical portions 415 and 425. In this case, the metal compound may be a compound including a metal such as Co, Ni, or Mn, or may be a compound including a precious metal oxide. The term "precious metal" refers to the second and third row transition metals of Groups 9, 10, and 11 of the periodic Table. The precious metals include Rh, Ir, Pd, Pt, Ag, or Au.

As a third example, when the energy supplied to the ceramic catalyst filter 100 is ion energy, the catalytic material may be a metal compound capable of ozone oxidation, for example, $MnO_2$ or $ZnO_2$. The ion energy may be, for example, plasma energy.

As a fourth example, when thermal energy is applied to the ceramic catalyst filter 100, the catalytic material may be a metal compound capable of a low-temperature oxidation reaction. In one example, the metal compound may be a compound including Cu, Co, Ni, Fe, Al, Si, or a precious metal. The low-temperature oxidation reaction refers to an oxidation reaction occurring between room temperature and 100° C. The thermal energy may include, for example, infrared energy or energy supplied from any radiative or conductive heat source.

The energy supplied to the ceramic catalytic filter 100 may be energy that causes a gas component present in the material 130 to undergo catalytic reaction upon the application of an activating energy to at least a portion of the horizontal portion 410 and/or a portion of the vertical portions 415 and 425. By application of such energy, a catalyst layer may be formed on a surface of the ceramic catalyst filter 100. The catalyst layer may be a side surface or a bottom surface of the second groove or channel 120. This catalyst layer is a region (layer) activated by the energy supply. The gas component included in the material 130 is decomposed or degraded due to the catalytic reaction as the gas component comes in contact with the catalyst layer (for example, by reacting with oxygen if exposed to light energy). The gas component may be a volatile organic compound (VOC) or other harmful gas. The volatile organic compound may be, for example, formaldehyde, acetaldehyde, ammonia, toluene, or acetic acid.

Figure 17:
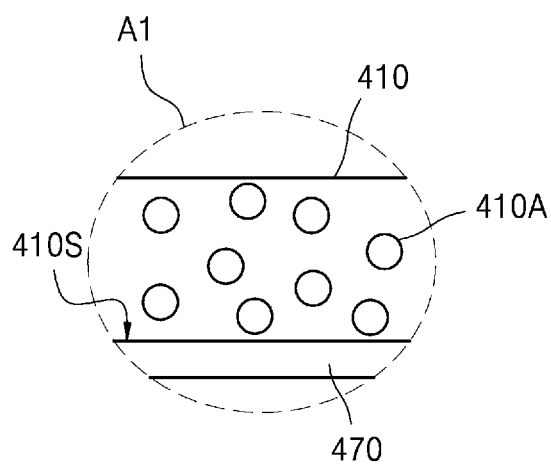
FIG. 17 is an enlarged cross-sectional view of a first portion A1 of FIG. 16.

FIG. 17 illustrates an enlarged cross-sectional view of the first portion A1 of FIG. 16. Referring to FIG. 17, the horizontal portion 410 includes pores 410A. In an example, the vertical portions 415 and 425 may not include pores.

In another example, the vertical portions 415 and 425 may also include pores, but the pore density of the vertical portions 415 and 425 may be less than that of the horizontal portion 410.

In another example, the first vertical portion 415 may include pores, and the second vertical portion 425 may not include pores.

In another example, the first and second vertical portions 415 and 425 include pores, and the pore density of the second vertical portion 425 may be less than that of the first vertical portion 415.

Referring to FIG. 17, a catalyst layer 470 including the above-described photocatalyst for air purification is provided on the surface 410S of the horizontal portion 410 to which an activating energy is applied. The material of the horizontal portion 410 may be different from the material of the catalyst layer 470 present on at least a portion of the surface 410S of the horizontal portion 410 irradiated with the energy. The horizontal portion 410 may be formed of a ceramic material different from the material of the catalyst layer 470. Alternatively, the horizontal portion 410 may be formed of a catalytic material different from the material of the catalyst layer 470. For example, the horizontal portion 410 may be formed of a catalytic material that is different from the material of the catalyst layer 470 and may be activated by one (for example, thermal energy) selected from the above-described four types of energy. In such an instance, energy capable of activating the catalyst layer 470 and two other types of energy may be used for activating the horizontal portion 410. Moreover, the different types of activating energy may be simultaneously supplied.

Figure 18:
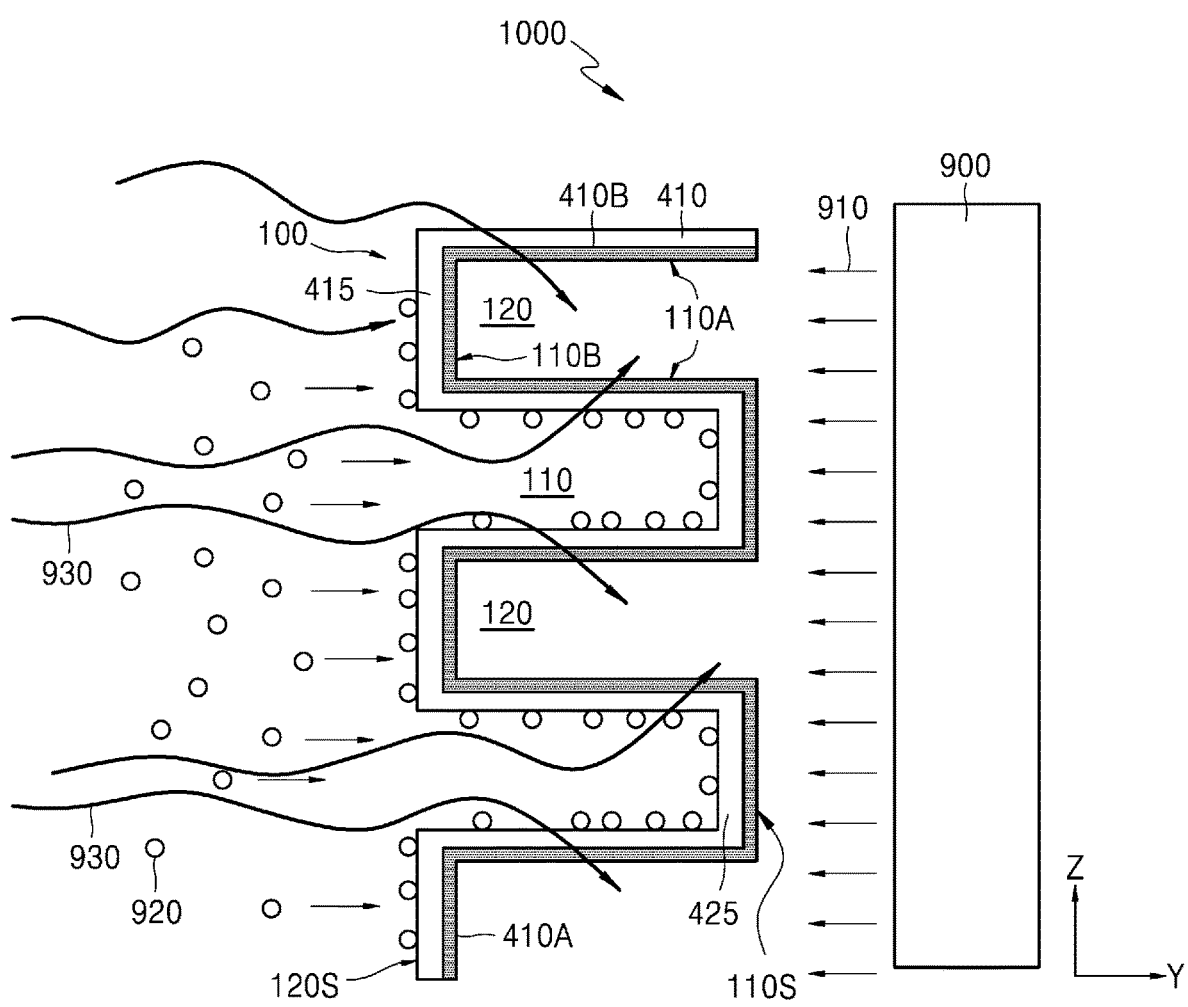
FIG. 18 is a cross-sectional view of a filtering system including the ceramic catalyst filter according to the embodiment.

FIG. 18 illustrates a cross-sectional view of a filtering system including the ceramic catalyst filter according to the embodiment.

Referring to FIG. 18, a filtering system 1000 includes a ceramic catalyst filter 100 and an energy supply unit 900. The energy supply unit 900 generates energy to activate a surface of the ceramic catalyst filter 100 through which air is discharged, that is, a surface directly exposed to energy supplied from the energy supply unit 900. The energy 910 generated from the energy supply unit 900 is applied to the side surface 110A and bottom surface 110B of the second groove or channel 120 and the second surface 110S of the ceramic catalyst filter 100. Since the above-described catalyst layer 410B is formed on the side surface 110A and bottom surface 110B of the second groove or channel 120, and the second surface 110S, the side surface 110A and bottom surface 110B of the second groove or channel 120, and the second surface 110S, may be irradiated or applied with such energy, and thus, may be activated.

In the filtering system having such a mechanism, a filtering process of a first material 920 and a second material 930 that flows into the ceramic catalyst filter 100, will be described. The first material 920 may include a particulate material. For example, the first material 920 may include particles. The particles may be, for example, particles having a particle diameter of 10 micrometers (μm) or less, that is, fine particles of PM10 or less. The fine particles may contain, for example, fine dust. The second material 930 may include a gaseous material, for example, the above-described volatile organic compound (VOC). The second material 930 may include an organic compound. The particulate first material 920 does not pass through the horizontal portion 410, which disposed between the first and second grooves or channels 110, 120, does not pass through the first and second vertical portions 415 and 425, and accumulates on a wall of the first groove or channel 110. The side surface and bottom surface of the first groove or channel 110 and the first surface 120S of the first vertical portion 415 may be collectively referred to as a first surface of the ceramic catalyst filter 100 that filters the first material 920.

At least the horizontal portion 410 of the ceramic catalyst filter 100 may be a porous material layer including pores 140A. Accordingly, the gaseous second material 930 may flow into the second groove 120 through at least the horizontal portion 410, that is, the sidewall of the first groove or channel 110. During this process, the second material 930 may be decomposed or degraded by causing a catalytic reaction while passing through a catalyst layer 410B. For example, when the second material 930 includes formaldehyde, the formaldehyde may be decomposed into water and carbon dioxide ($CO_2$) by a catalytic reaction with oxygen, and which takes place in the second groove or channel 120 while passing through the catalyst layer 410B. In this way, formaldehyde may be removed, e.g., from air.

Meanwhile, the energy supplied from the energy supply unit 900 may include a light energy supply source for supplying light energy in a visible light band, an ultraviolet light band, an ion energy supply source for supplying plasma, or a thermal energy supply source for supplying infrared light as thermal energy. When plasma is supplied, the second material 930 may be decomposed by causing a catalytic reaction with ozone present in the second groove or channel 120.

Meanwhile, the photocatalyst for air purification according to an embodiment may be prepared by the following method.

A method of preparing the photocatalyst for air purification according to an embodiment includes: conducting a first heat treatment of a mixture including a precursor of a first metal oxide particle having ultraviolet absorptivity, and a precursor of second metal oxide particles to obtain a first product; adding glucose and sodium hydroxide to the first product and conducting second heat treatment to obtain a second product; and fluorinating a surface of the second product.

According to an embodiment, the photocatalyst for air purification may be prepared through impregnation using glucose and sodium hydroxide (NaOH) and surface fluorination.

The second metal oxide particles may be supported on the photocatalyst by impregnation using glucose and sodium hydroxide (NaOH), thereby enhancing the light absorption rate and charge pair separation efficiency of the catalyst.

According to an embodiment, the content of the precursor of the second metal oxide particle may be about 0.1 parts by weight to about 5 parts by weight based on 100 parts by weight of the first metal oxide particle.

According to an embodiment, based on 1 mole of copper supported on the first product, the glucose is added in an amount of about 2 moles to about 6 moles, and the sodium hydroxide is added in an amount of 2 moles to 16 moles.

The first heat treatment and the second heat treatment may be performed by bath treatment. The catalyst may be synthesized by impregnation as a result of the bath treatment.

The fluorinating of the surface of the second product may include using sodium fluoride (NaF). Sodium fluoride (NaF) is less toxic than hydrogen fluoride (HF), so the use of harmful materials in the process can be avoided. A photocatalyst capable of effectively removing/decomposing/degrading VOCs and viruses through surface fluorination may be obtained by using sodium fluoride (NaF).

Hereinafter, exemplary embodiments will be described in more detail through Examples and Comparative Examples. However, these Examples are for illustrating the technical ideas of the present disclosure, and the scope of the present disclosure is not limited thereto.

EXAMPLES

Evaluation Example 1: Evaluation of Effect of Copper as Cocatalyst

In order to check the appropriate oxidation state and content range of a metal oxide to be supported, $Cu_2O/TiO_2$ catalysts were synthesized and tested using an impregnation process as follows.

$CuCl_2$ was mixed with 100 parts by weight of $TiO_2$ (ST-01, ISHIHARA SANGYO KAISHA, LTD.) in different amounts of 0.1, 0.5, 1, 2, and 5 parts by weight, and then bath treatment was performed at 90° C. for 1 hour to obtain a $CuO/TiO_2$ containing solution (the preparation of five different first solutions).

Glucose (in mol % ratio, Cu:glucose=1:4) and NaOH (in mol %, Cu:NaOH=1:2, 1:4, 1:8, and 1:16) were added to the $CuO/TiO_2$ containing solution (first solutions), respectively, and then bath treatment was performed at 90° C. for 1 hour to obtain a $Cu_2O/TiO_2$ containing solution (second solutions).

The $Cu_2O/TiO_2$ containing solution (second solutions) were dried in an oven at 110° C. overnight, and then the dried product was ground with a mortar to obtain the various $Cu_2O/TiO_2$ catalysts.

Figure 2:
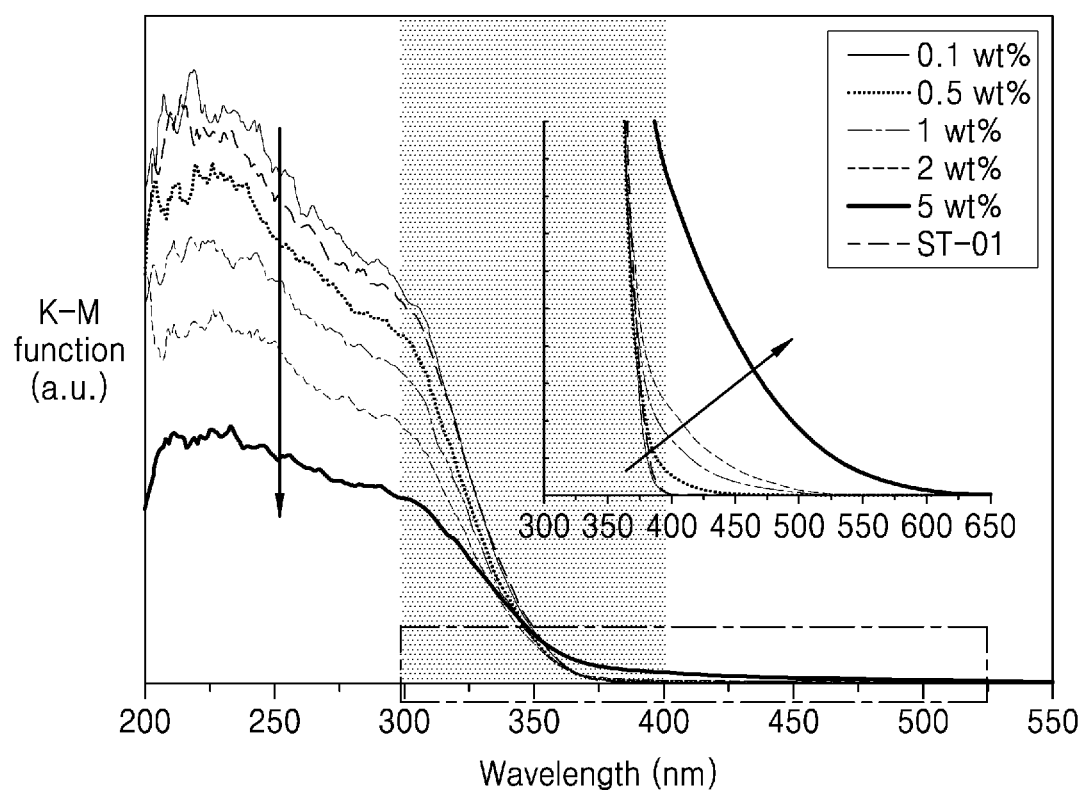
FIG. 2 illustrates a K-M (Kubelka-Munk) function plot vs. wavelength according to the concentration of Cu in the $Cu_2O/TiO_2$ photocatalyst of Evaluation Example 1.
Figure 3:
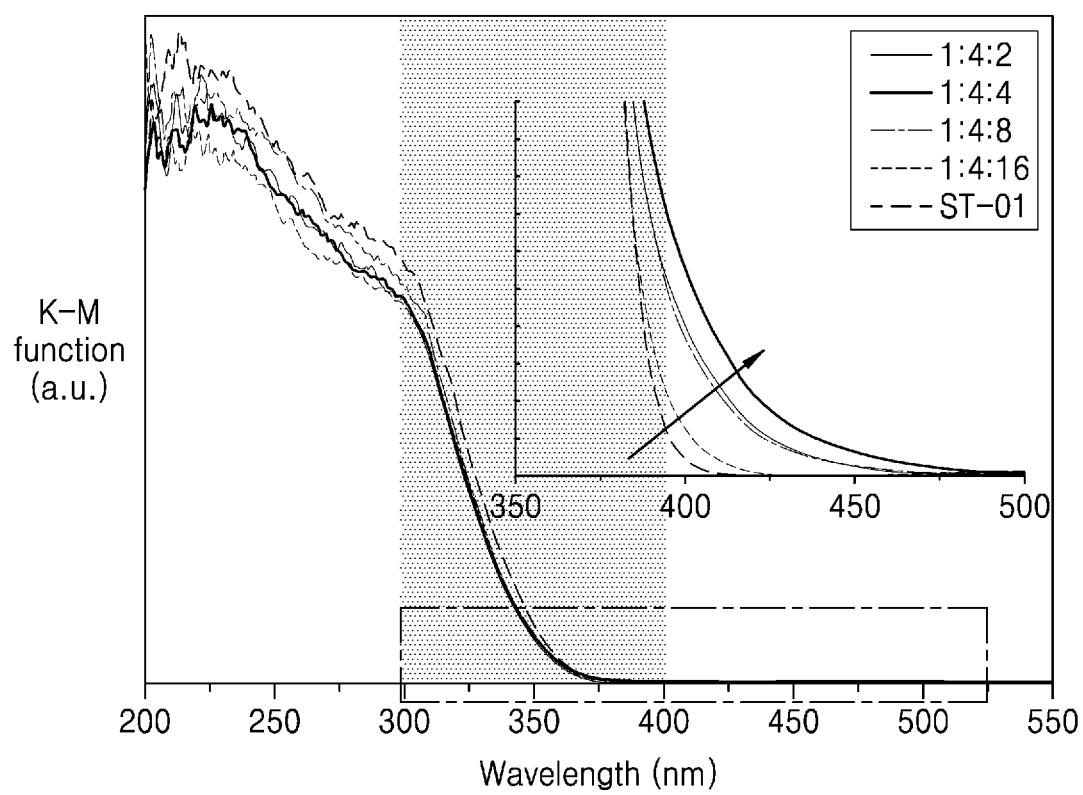
FIG. 3 illustrates a K-M (Kubelka-Munk) function plot vs. wavelength according to the composition ratio of Cu:glucose:NaOH in the $Cu_2O/TiO_2$ photocatalyst of Evaluation Example 1.

In order to confirm the effect of copper as a cocatalyst in the synthesized $Cu_2O/TiO_2$ catalyst, the change in absorbance of the $Cu_2O/TiO_2$ catalyst according to the Cu content and the composition ratio of Cu:glucose:NaOH was measured using a Solidspec-3700 device, a K-M (Kubelka-Munk) function graph for each wavelength according to the content of Cu as illustrated in FIG. 2. A K-M (Kubelka-Munk) function plot vs. wavelength according to the composition ratio of Cu:glucose:NaOH is illustrated in FIG. 3.

As shown in FIG. 2, at a wavelength range of 350 nm or more, the absorbance of the $Cu_2O/TiO_2$ catalyst tends to increase as the content of Cu increases. However, in the wavelength range of about 300 nm to about 350 nm, an opposite tendency appears, so it may be understood that, when considering a desired wavelength range (about 300 nm to 400 nm), Cu exhibits the most preferable absorbance at 0.5 parts by weight. On the other hand, as shown in FIG. 3, when the composition ratio of Cu:glucose:NaOH was 1:4:4, the light absorption rate was the highest.

Figure 4:
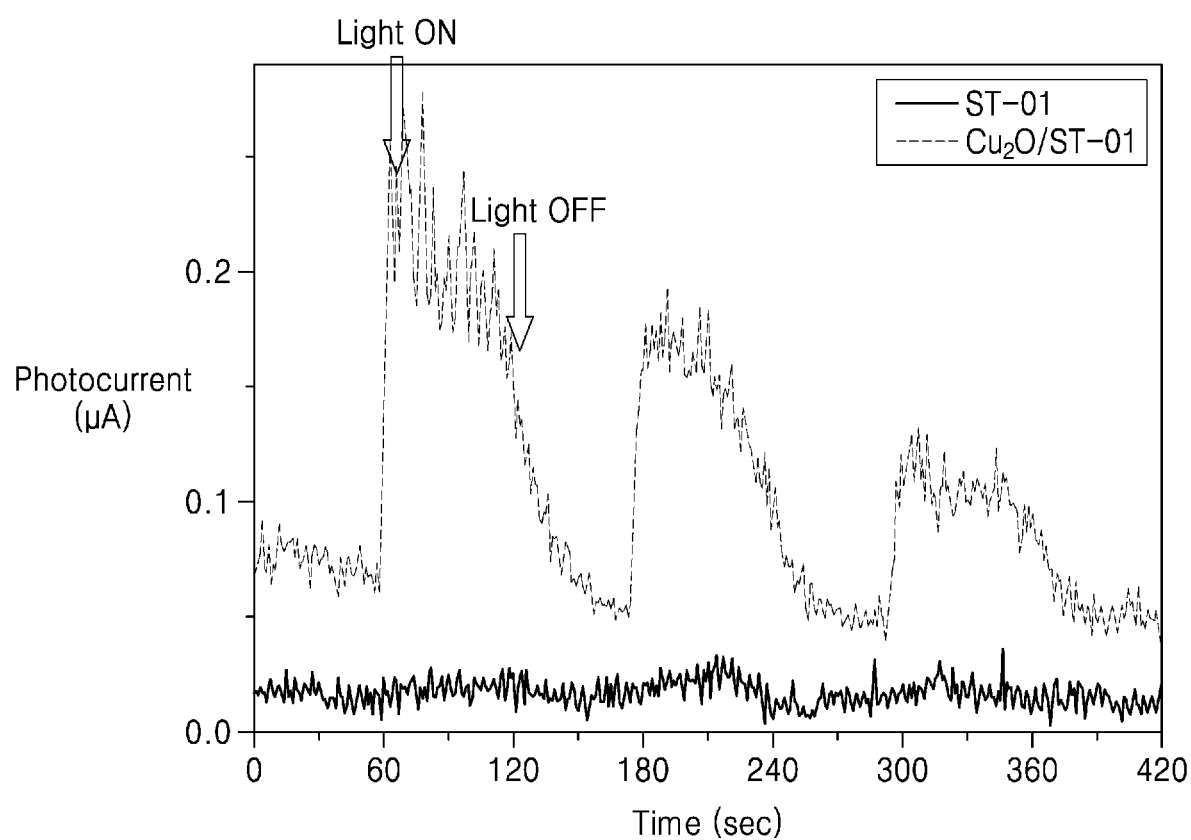
FIG. 4 illustrates the results of measuring the on-off photocurrent generated by irradiation of the $Cu_2O/TiO_2$ photocatalyst with ultraviolet light of in Evaluation Example 1.
Figure 5:
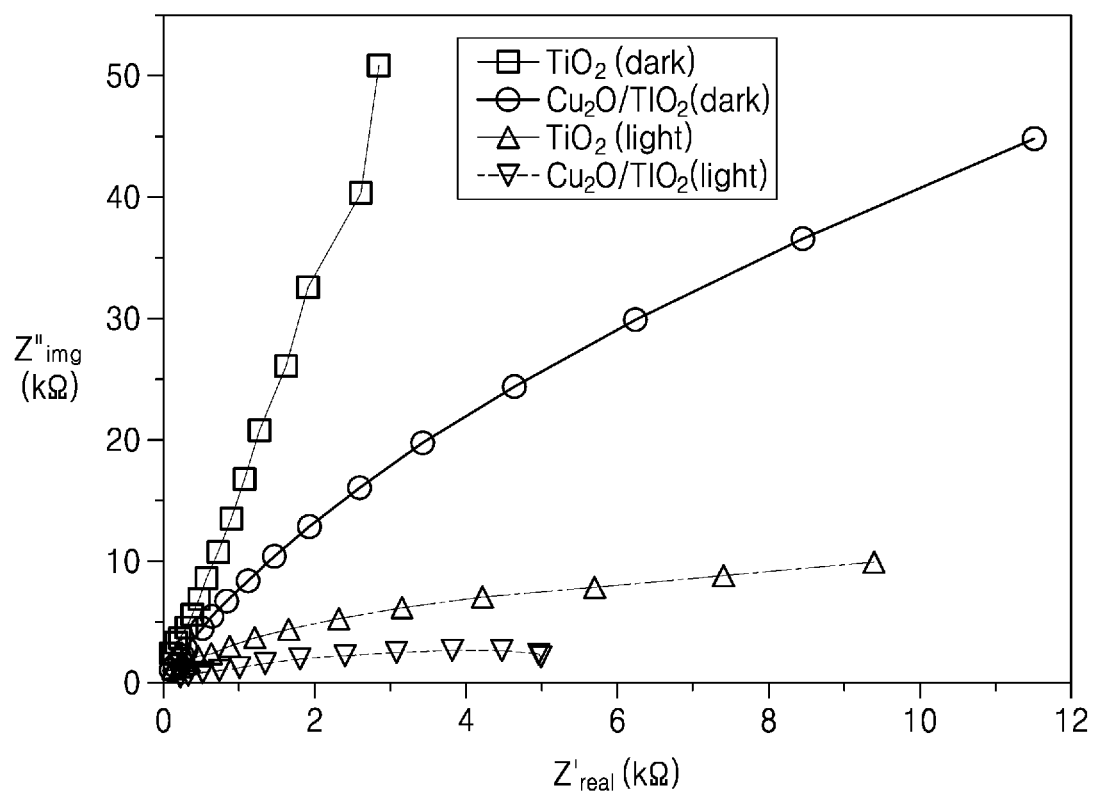
FIG. 5 illustrates the results of measuring the resistance of the $Cu_2O/TiO_2$ photocatalyst of Evaluation Example 1 before (dark) and after (light) irradiation with ultraviolet light.

FIG. 4 illustrates the results of measuring the photocurrent generated by the exposure of the $Cu_2O/TiO_2$ catalyst to ultraviolet light, and FIG. 5 illustrates the results of measuring the resistance of the $Cu_2O/TiO_2$ catalyst before and after irradiation with ultraviolet light. As shown in FIGS. 4 and 5, the supported copper improves the absorption rate of light, prevents recombination of charge pairs by absorbing electrons generated by ultraviolet light, and facilitates charge transfer by lowering the resistance of the catalyst.

Figure 6:
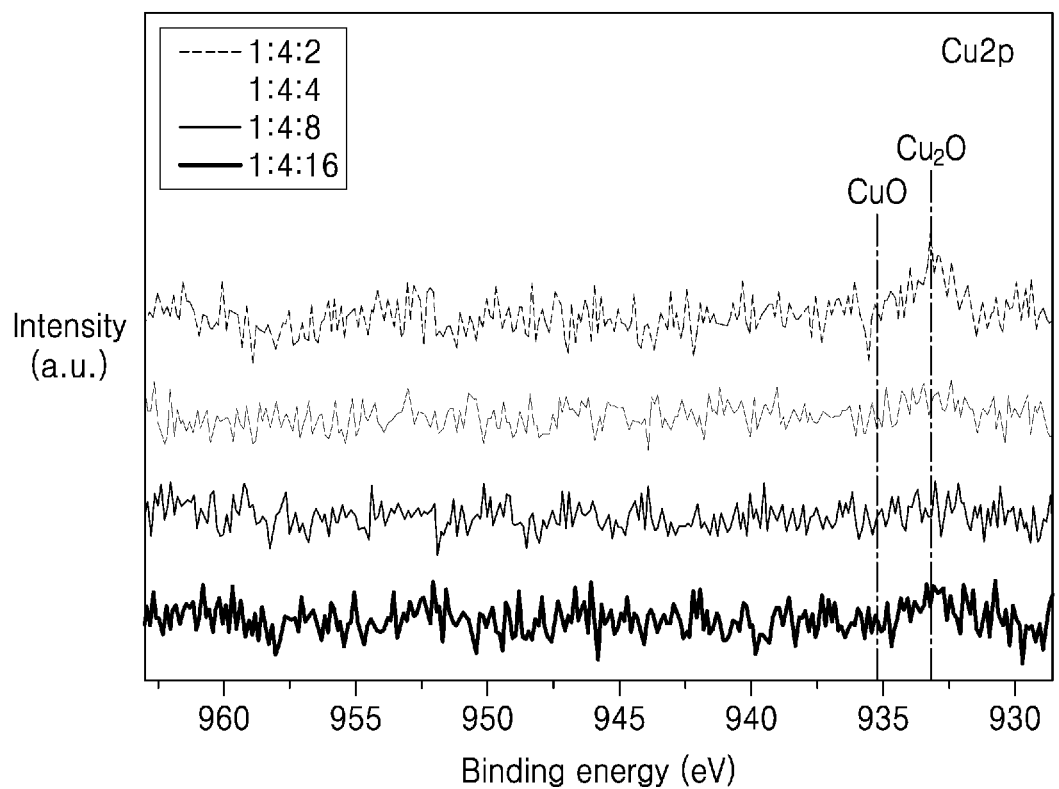
FIG. 6 illustrates the results of measuring the binding energy of the $Cu_2O/TiO_2$ photocatalyst of Evaluation Example 1 according to the composition ratio of Cu:glucose: NaOH.
Figure 7:
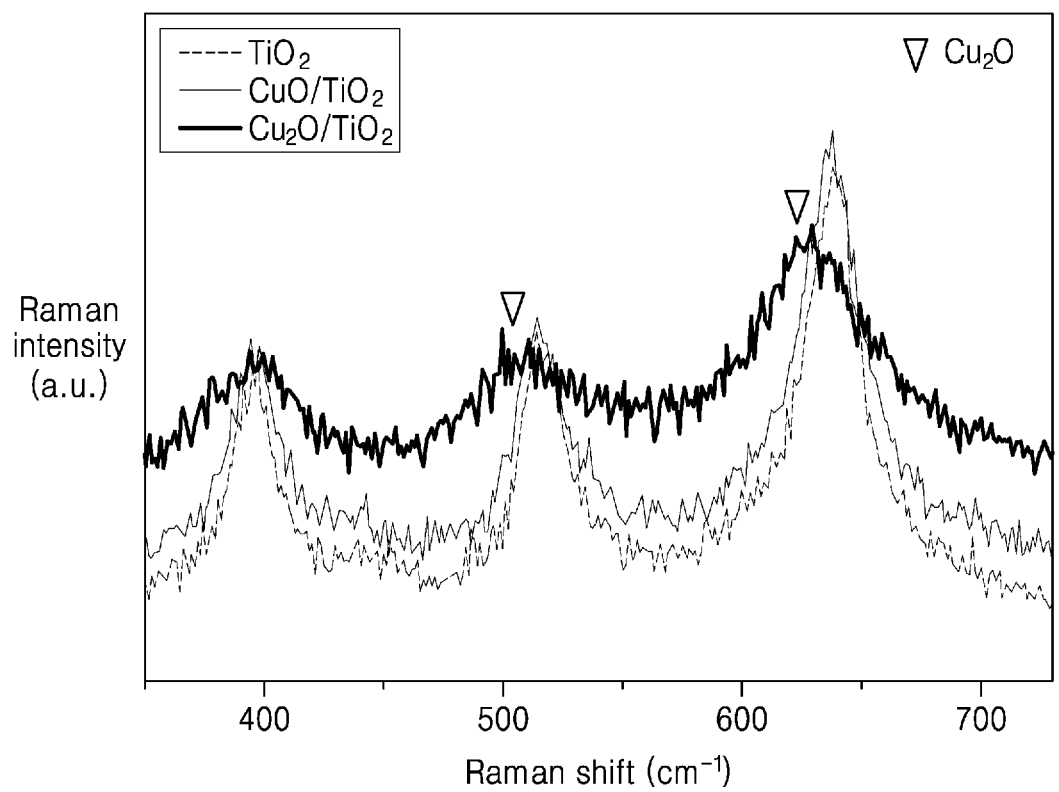
FIG. 7 illustrates a Raman spectrum of the $Cu_2O/TiO_2$ (copper(I)) photocatalyst of Evaluation Example 1 compared to a Raman spectrum of a $CuO/TiO_2$ (copper(II)) photocatalyst and the Raman spectrum of a $TiO_2$ support.

In order to check the oxidation state of copper in the synthesized $Cu_2O/TiO_2$ catalyst, the binding energy and Raman spectrum were measured for the $Cu_2O/TiO_2$ catalyst, and the results are illustrated in FIGS. 6 and 7 respectively. FIG. 6 illustrates the results of measuring the binding energy of the $Cu_2O/TiO_2$ catalyst according to the composition ratio of Cu:glucose:NaOH, and FIG. 7 illustrates a Raman spectrum of the $Cu_2O/TiO_2$ catalyst together with a Raman spectrum of the $CuO/TiO_2$ catalyst and a Raman spectrum of a $TiO_2$ support. The $CuO/TiO_2$ catalyst was obtained by drying the $CuO/TiO_2$ containing solution (first solution) in an oven at 110° C. overnight and then grinding the dried resulting product with a mortar and pestle. As shown in FIGS. 6 and 7, the synthesized catalyst is not CuO but $Cu_2O$.

Evaluation Example 2: Evaluation of Surface Area Effect of Carrier

A carrier exhibits a difference in surface area depending on the type of carrier. In order to check the surface area of a carrier, a photocatalyst was manufactured using ST-01 (ISHIHARA SANGYO KAISHA, LTD.) and P25 (PlasmaChem GmbH) having different surface areas among commercially available $TiO_2$ products.

$CuCl_2$ was mixed with 100 parts by weight of $TiO_2$ with each of ST-01 and P25 in an amount of 0.5 parts by weight, followed by a bath treatment at 90° C. for 1 hour to obtain a $CuO/TiO_2$ containing solutions. Glucose and NaOH (in mol % ratio, Cu:glucose:NaOH=1:4:4) was added to the $CuO/TiO_2$ containing solutions, and then bath treatment was performed at 90° C. for 1 hour to obtain a $Cu_2O/TiO_2$ containing solutions. The $Cu_2O/TiO_2$ containing solutions were dried in an oven at 110° C. overnight, and then the product was ground with a mortar and pestle to obtain a $Cu_2O/TiO_2$ catalyst.

Figure 8:
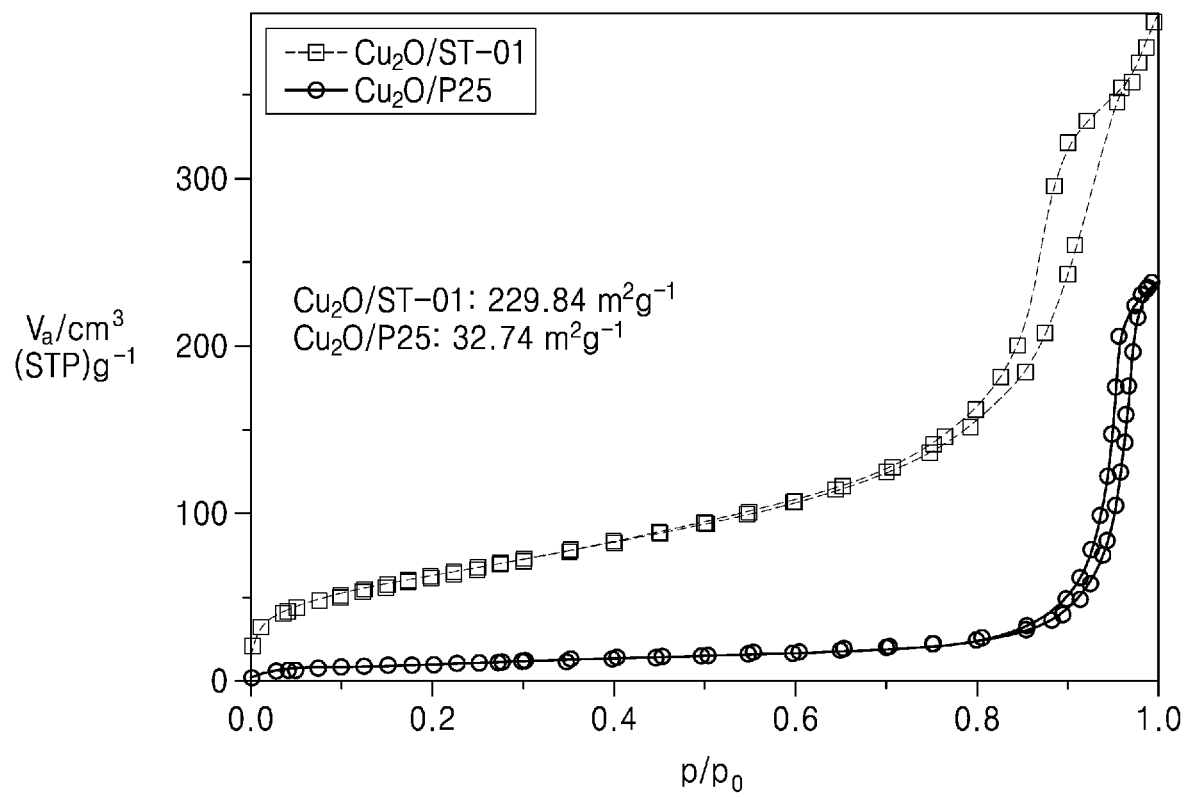
FIG. 8 illustrates the results of measuring the specific surface area of the $Cu_2O/TiO_2$ catalyst supported on each of ST-01 and P25 synthesized in Evaluation Example 2.

FIG. 8 illustrates the results of measuring the specific surface area of the $Cu_2O/TiO_2$ catalysts supported on ST-01 and P25. As shown in FIG. 8, the surface area of the catalyst ($Cu_2O$/ST-01) in which the copper is supported on ST-01 is about 230 $m^2/g$, and the surface area of the catalyst ($Cu_2O$/P25) in which copper is supported on P25 is about 33 $m^2/g$. Notably there is a 7-fold difference in surface area. Because a metal catalyzed reaction primarily occurs on the surface of a catalyst, a person of skill would generally expect that the reaction area of the catalyst would increase as the surface area of the catalyst increases.

Figure 9:
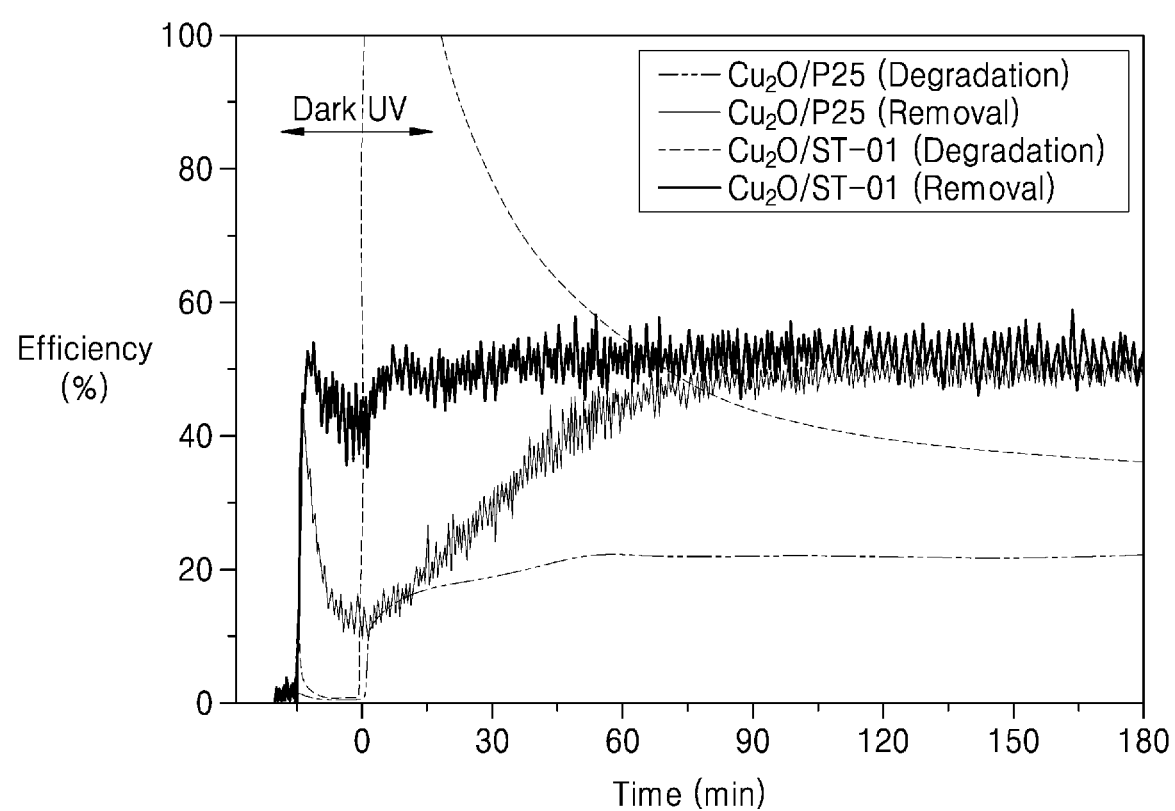
FIG. 9 illustrates the results of measuring the VOC removal and decomposition efficiency over time for the $Cu_2O/TiO_2$ photocatalyst supported on each of ST-01 and P25 of Evaluation Example 2.

FIG. 9 illustrates the results of measuring the VOC removal and decomposition efficiency over time for the $Cu_2O/TiO_2$ catalyst supported on each of ST-01 and P25. The VOC removal and decomposition efficiency was measured by determining the amount of $CO_2$ generated upon exposure of the catalyst with ultraviolet light after confirming the extent to which VOC is adsorbed onto a surface of the catalyst, by measurement of desorption in a dark reaction for 15 minutes prior to the exposure to the light. In the experiment, light was applied with an intensity of 50 milliwatts per square centimeter ($mW/cm^2$) after fixing the catalyst in a 2×2 $cm^2$ holder. The gas flow rate is 500 mL/min, and an initial concentration of VOC is 20 ppm is used. As shown in FIG. 9, the VOC adsorption efficiency of the catalyst ($Cu_2O$/ST-01) in which copper is supported on ST-01 (larger surface area) increases and the decomposition efficiency also increases.

Evaluation Example 3: Evaluation of Effect of Fluorination on Surface of Catalyst The $Cu_2O/TiO_2$ catalyst synthesized in Evaluation Example 1 was introduced into a 30 millimolar (mM) NaF (pH 3.5) solution, followed by stirring for 30 minutes and then filtering to prepare a F—$Cu_2O/TiO_2$ catalyst having a fluorinated surface.

Figure 10:
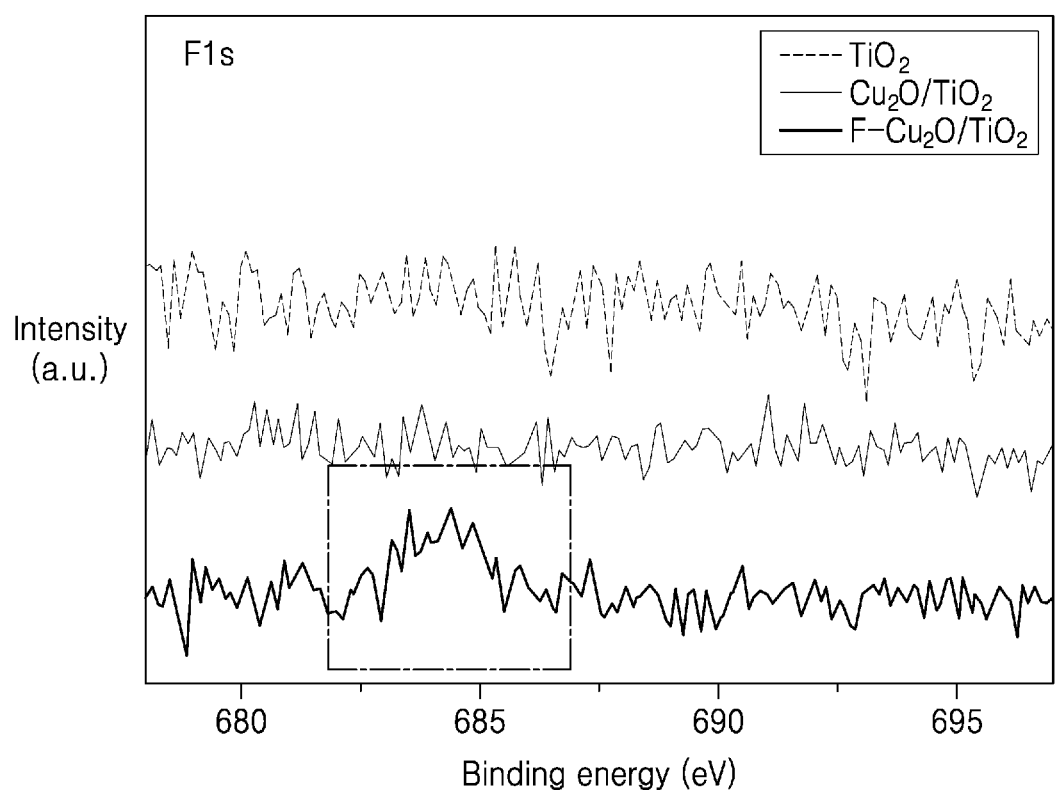
FIG. 10 illustrates the results of measuring the binding energy of the surface-fluorinated F—$Cu_2O/TiO_2$ photocatalyst of Evaluation Example 3.
Figure 11:
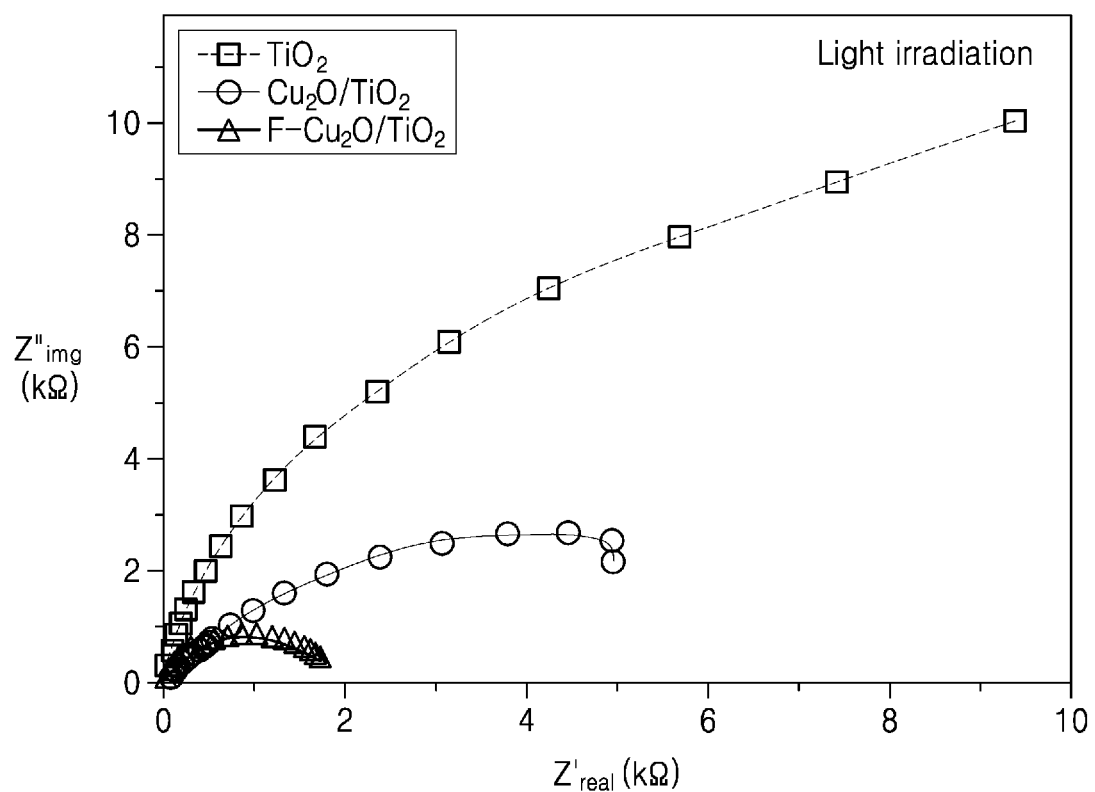
FIG. 11 illustrates the results of measuring the resistance of the surface-fluorinated F—$Cu_2O/TiO_2$ photocatalyst of Evaluation Example 3, upon irradiation with ultraviolet light.
Figure 12:
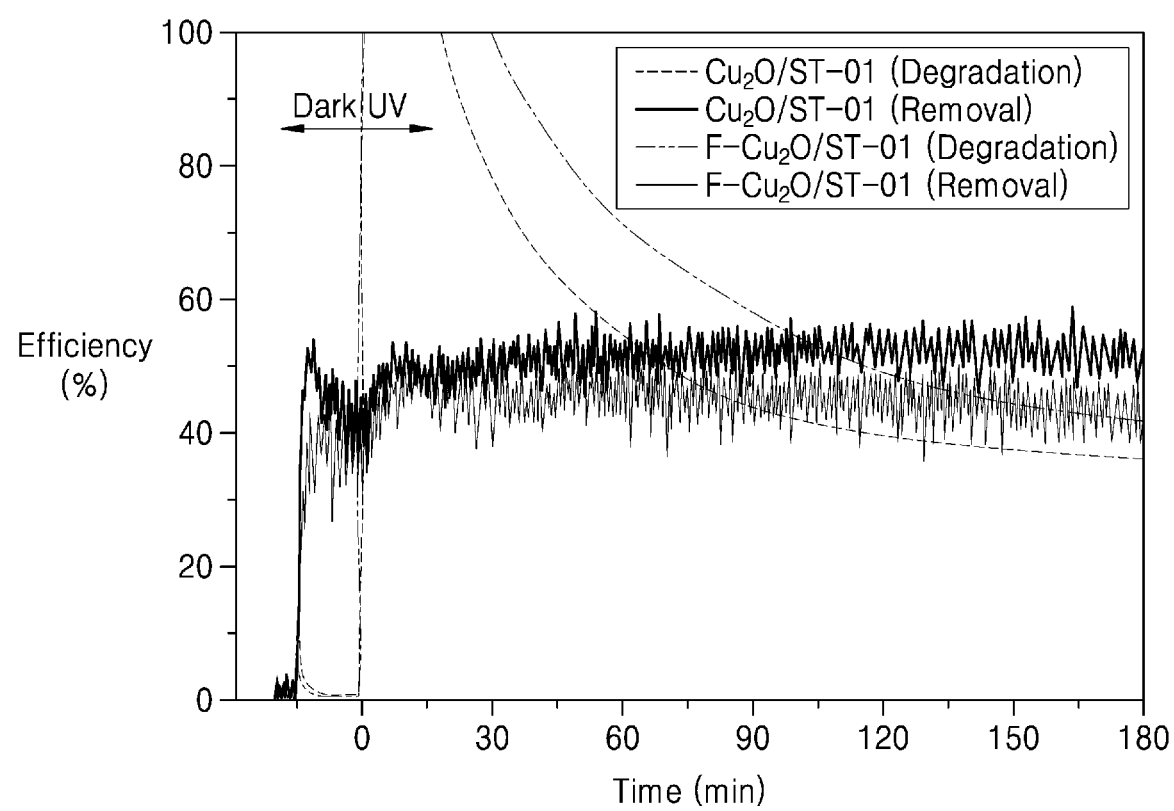
FIG. 12 illustrates the results of measuring VOC removal and decomposition efficiency of the surface-fluorinated F—$Cu_2O/TiO_2$ photocatalyst of Evaluation Example 3.

FIGS. 10 and 11 illustrate the results of measuring the binding energy and resistances of $TiO_2$ as a carrier, the $Cu_2O/TiO_2$ catalyst, and the F—$Cu_2O/TiO_2$ catalyst, respectively. FIG. 12 illustrates the results of measuring the VOC removal and decomposition efficiencies of the $Cu_2O/TiO_2$ catalyst and the F—$Cu_2O/TiO_2$ catalyst over time.

As shown in FIGS. 10 and 11, the F—$Cu_2O/TiO_2$ catalyst with fluoride bound to the catalyst surface, and when exposed to the light, the resistance of the catalyst decreases, which facilitates the transfer of charges. Further, as shown in FIG. 12, it may be found that the VOC decomposition efficiency of the F—$Cu_2O/TiO_2$ catalyst is increased by the surface treatment with fluoride. The surface treatment with fluoride not only increases VOC decomposition efficiency by increasing the generation of ROS, but also removes VOC and inhibits adsorption of the resulting intermediates on the surface of the catalyst, thereby continuously removing/decomposing VOC.

The results of comparing the VOC removal and decomposition efficiency using each catalyst are summarized in Table 1 below.

TABLE 1

| | Efficiency (%) | | |
|---|---|---|---|
| Catalyst | Removal | Decomposition | Decomposition/removal |
| P25 | 58.0 | 19.6 | 33.8 |
| ST-01 | 58.4 | 16.4 | 28.1 |
| $Cu_2O$/P25 | 50.3 | 21.9 | 43.5 |
| $Cu_2O$/ST-01 | 51.9 | 36.3 | 69.9 |
| F—$Cu_2O$/ST-01 | 44.1 | 42.4 | 96.1 |

Evaluation Example 4: Evaluation of Virus Removal Effect

The virus removal effects of the $Cu_2O/TiO_2$ catalyst of Evaluation Example 1 and the F—$Cu_2O/TiO_2$ catalyst of Evaluation Example 3 were measured, and the results are shown in Table 2. The virus removal effect is determined using an experimental result of a dark reaction (without light), and is expressed as removal efficiency with respect to the catalyst adsorption of virus. Specifically, the virus removal effect was analyzed by CPE (cytopathic effect)/MTT (3-(4,5-dimethythiazol-2-yl)-2,5-diphenyl tetrazolium bromide) method in combination with microscopic observation.

TABLE 2

| Catalyst | Catalyst concentration | Types of viruses | Initial virus concentration (CCID50/well) | Removal efficiency (%) | |
|---|---|---|---|---|---|
| | | | | 10 minutes | 5 hours |
| ST-01 | 2.5 mg/L | Influenza A | 180,000 | 98.45 | 98.45 |
| $Cu_2O$/ST-01 | 2.5 mg/L | Influenza A | 180,000 | 99.99 | 99.99 |
| F—$Cu_2O$/ST-01 | 2.5 mg/L | Influenza A | 180,000 | 99.99 | 99.99 |

As shown in Table 1 above, it may be found that the catalysts may be applicable for removing viruses. Further, it may be found that the virus removal efficiency is improved in the $Cu_2O$/ST-01 and F—$Cu_2O$/ST-01 catalysts as compared with ST-01 alone.

When using a photocatalyst for air purification according to an embodiment, volatile organic compounds (VOCs) and viruses may be effectively and continuously removed/decomposed/degraded. The photocatalyst for air purification may be applied to various indoor and outdoor air purification systems in the form of a filter.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A photocatalyst for air purification, comprising:
   a first metal oxide particle having ultraviolet absorptivity, and fluorine bound to a surface of the first metal oxide particle; and
   second metal oxide particles present on the surface of the first metal oxide particle.

2. The photocatalyst for air purification of claim 1, wherein the fluorine bound to the surface of the first metal oxide particle is present in a region other than a region in which the second metal oxide particles are present, and the fluorine is not present at an interface between the first metal oxide particle and the second metal oxide particles.

3. The photocatalyst for air purification of claim 1, wherein the first metal oxide particle includes a metal oxide of titanium (Ti), zinc (Zn), zirconium (Zr), tantalum (Ta), niobium (Nb), tungsten (W), or an alloy of metal oxides thereof.

4. The photocatalyst of claim 1, wherein the first metal oxide particle includes titanium oxide.

5. The photocatalyst of claim 1, wherein the first metal oxide particle has a specific surface area of about 20 square meters per gram to about 300 square meters per gram.

6. The photocatalyst of claim 1, wherein the first metal oxide particle is primary particle, or is a secondary particle in which primary particles are aggregated or bonded to another first metal oxide particle.

7. The photocatalyst of claim 1, wherein the second metal oxide particles further comprise at least one second metal oxides of copper (Cu), platinum (Pt), gold (Au), silver (Ag), zinc (Zn), palladium (Pd), or an alloy of metal oxides thereof, and the at least one second metal oxide particle is different from the first metal oxide particle.

8. The photocatalyst of claim 1, wherein the second metal oxide particles further comprise copper(I) oxide.

9. The photocatalyst of claim 1, wherein a content of the second metal oxide particles is about 0.1 parts by weight to about 5 parts by weight based on 100 parts by weight of the first metal oxide particle.

10. The photocatalyst of claim 1, wherein at least a majority of first metal oxide particles, and a majority of second metal oxide particles, independently have a spherical shape, a tubular shape, a rod shape, a fiber shape, a sheet shape, a conical shape, a pyramidal shape, a toroidal shape, or any shape combination thereof.

11. The photocatalyst of claim 1, wherein the first metal oxide particle is a microscale primary particle or a microscale secondary particle, the second metal oxide particle is a nanometer-scale primary particle, and the surface of the first metal oxide particle is surrounded by the second metal oxide particles.

12. The photocatalyst of claim 1, wherein the photocatalyst photo-catalyzes in an ultraviolet wavelength range.

13. The photocatalyst of claim 1, wherein the fluorine is bonded to the surface of the first metal oxide particle.

14. A photocatalyst film comprising the photocatalyst of claim 1.

15. An air purification device comprising the photocatalyst of claim 1.

16. A ceramic catalyst filter comprising:
   a monolithic structure having a first surface that blocks a first material and that provides transmission of a second material, and a second surface from which the second material is removed,
   wherein the second surface of the monolithic structure comprises a catalyst layer including the photocatalyst of claim 1 for removing the second material upon exposure of the photocatalyst to ultraviolet light.

17. A method of preparing the photocatalyst of claim 1, the method comprising:
   conducting a first heat treatment of a mixture including a precursor of a first metal oxide particle having ultraviolet absorptivity, and a precursor of second metal oxide particles, to obtain a first product;
   adding glucose and sodium hydroxide to the first product and conducting a second heat treatment to obtain a second product; and
   fluorinating a surface of the second product.

18. The method of claim 17, wherein a content of the precursor of the second metal oxide particles is about 0.1 parts by weight to about 5 parts by weight based on 100 parts by weight of the first metal oxide particle.

19. The method of claim 17, wherein the adding of the glucose and the sodium hydroxide comprises adding about 2 moles to about 6 moles of the glucose and about 2 moles to about 16 moles of the sodium hydroxide, based on 1 mole of copper of the first product.

20. The method of claim 17, wherein the fluorinating of the surface of the second product comprises an addition of sodium fluoride (NaF).

* * * * *